US006019746A

United States Patent [19]

Picha et al.

[11] Patent Number: 6,019,746

[45] Date of Patent: Feb. 1, 2000

[54] LOW PROFILE BALLOON FEEDING DEVICE

[75] Inventors: George J. Picha, Independence; Anthony J. Szpak, Parma, both of Ohio

[73] Assignee: Applied Medical Technology, Inc., Cleveland, Ohio

[21] Appl. No.: 08/857,731

[22] Filed: May 16, 1997

Related U.S. Application Data

[60] Provisional application No. 60/018,374, May 17, 1996.

[51] Int. Cl.$^{7}$ .............................................. A61M 5/32

[52] U.S. Cl. ............................ 604/175; 604/96; 604/256

[58] Field of Search ............................ 604/96–102, 256, 604/246, 247, 174, 175; 600/29–32

[56] References Cited

U.S. PATENT DOCUMENTS

| | | | |
|---|---|---|---|
| 5,125,897 | 6/1992 | Quinn et al. | 604/99 |
| 5,342,321 | 8/1994 | Potter | 604/174 |
| 5,411,491 | 5/1995 | Goldhardt et al. | 604/247 |
| 5,413,565 | 5/1995 | Michels et al. | 604/247 |
| 5,556,385 | 9/1996 | Anderson | 604/174 |
| 5,718,691 | 2/1998 | Russo | 604/247 |

*Primary Examiner*—Wynn Wood Coggins
*Assistant Examiner*—Deborah Blyveis
*Attorney, Agent, or Firm*—Pearne, Gordon, McCoy & Granger LLP

[57] ABSTRACT

A low profile gastrostomy feeding device having a bolster portion, a balloon member, and tubular member extending between the bolster portion and the balloon member. The bolster portion includes an anti-reflux valve, a closure member, an inflation valve housing, and a cap retainer portion. An inflation lumen and a feeding lumen are provided by the tubular member. The inflation lumen curves as it passes through the bolster portion from the tubular member to the inflation housing.

11 Claims, 4 Drawing Sheets

LOW PROFILE BALLOON FEEDING DEVICE

CROSS REFERENCE TO RELATED APPLICATIONS

This application claims the benefit of U.S. provisional application Ser. No. 60/018,374, filed May 17, 1996.

BACKGROUND OF THE INVENTION

The present invention is directed toward gastrostomy feeding appliances or devices and, more particularly, to gastrostomy devices, methods for manufacturing gastrostomy devices, and methods for securing gastrostomy devices to a patient.

Over the years, several different designs for gastrostomy feeding devices have been proposed. Each of these designs has an internal bolster, an external bolster, and a feeding conduit that extends from the external bolster toward or through the internal bolster. A valve is typically provided to prevent reflux of gastric fluid through the feeding conduit. The internal bolster prevents the feeding conduit from being withdrawn from the patient's stoma, and the external bolster provides means for connecting the feeding device with a food supply tube.

Generally, these prior art feeding device designs may be separated into two basic categories: those with fixed, non-expandable internal bolsters, and those with expandable or inflatable internal bolsters. With regard to the latter category, several problems have been encountered.

The prior art expanding bolster designs have not satisfied the conflicting requirements of such feeding devices. The inflatable bolster must be capable of selected inflation/deflation and must be inflated and deflated from an exterior of the patient's body. The exterior bolster should not protrude too far from the patient's body, both for the patient's comfort and to prevent the bolster from becoming snagged on the patient's clothes or other items. The air passageway or lumen connecting the interior balloon to the exterior, must not significantly increase the diameter or material thickness of the tubular member extending between the interior and exterior bolsters. The air passageway must not interfere with the food supply tube connecting means and must not weaken the overall device design. Finally, the internal and external bolsters must not interfere with placement or removal of the device.

Due to these competing interests, there exists a need in the art for a low profile balloon feeding or gastrostomy device which balances these conflicting requirements and which provides a readily usable and satisfactory design.

SUMMARY OF THE INVENTION

It is an object of the present invention to provide a low profile balloon feeding or gastrostomy device which is easily manufactured, installed and used. It is a further object of the present invention to provide such a feeding device wherein an air lumen is provided by a tubular member, and wherein the air lumen does not significantly increase the diameter of the tubular member.

In accordance with the present invention, a feeding device includes an elongated tubular member and an exterior bolster portion. The tubular member includes a feeding lumen and an inflation lumen, each of which extend longitudinally the length of the tubular member. The inflation lumen is in fluid communication with a balloon member that defines an internal bolster.

In further accordance with the present invention, the inflation passage and the feeding passage extend through the exterior bolster portion. At the union of the bolster portion and the tubular member, the feeding passage is closed by an anti-reflux or one-way check valve, and immediately above the valve, the feeding lumen defines a receptacle for a locking cap member.

In further accordance with the present invention, the external bolster includes the valve, a closure member, an inflation valve housing, and a cap retainer portion, at least some of which are provided by a continuous wall portion. The valve may be integrally formed with the bolster portion.

In further accordance with the present invention, the inflation passage curves as it passes through the bolster portion between the inflation valve housing and the tubular member. Curving of the inflation passage cooperates with the locking cap member receptacle to provide a generally constant thickness of material between the passage and the receptacle.

The inflation valve housing sealingly receives an inflation valve by means of which the balloon may be selectively inflated or deflated.

BRIEF DESCRIPTION OF THE DRAWINGS

These and further features of the present invention will be apparent with reference to the following description and drawings, wherein.

DETAILED DESCRIPTION OF THE PREFERRED EMBODIMENT

Figure 1B:
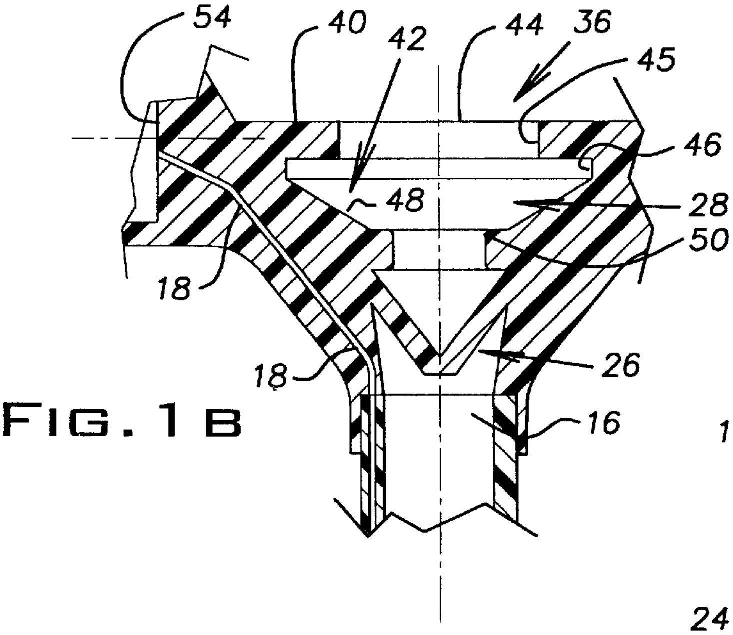
FIG. 1*b* is an enlarged sectional view of an anti-reflux valve of the feeding device shown in FIG. 1*a;*
Figure 1C:
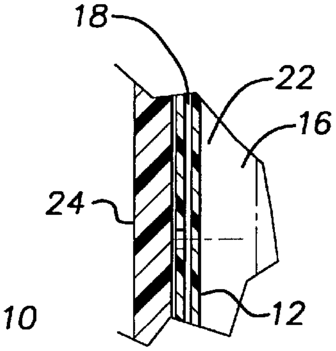
FIG. 1*c* is an enlarged sectional view of an intermediate portion of a tubular member of the feeding device shown in FIG. 1*a;*
Figure 1A:
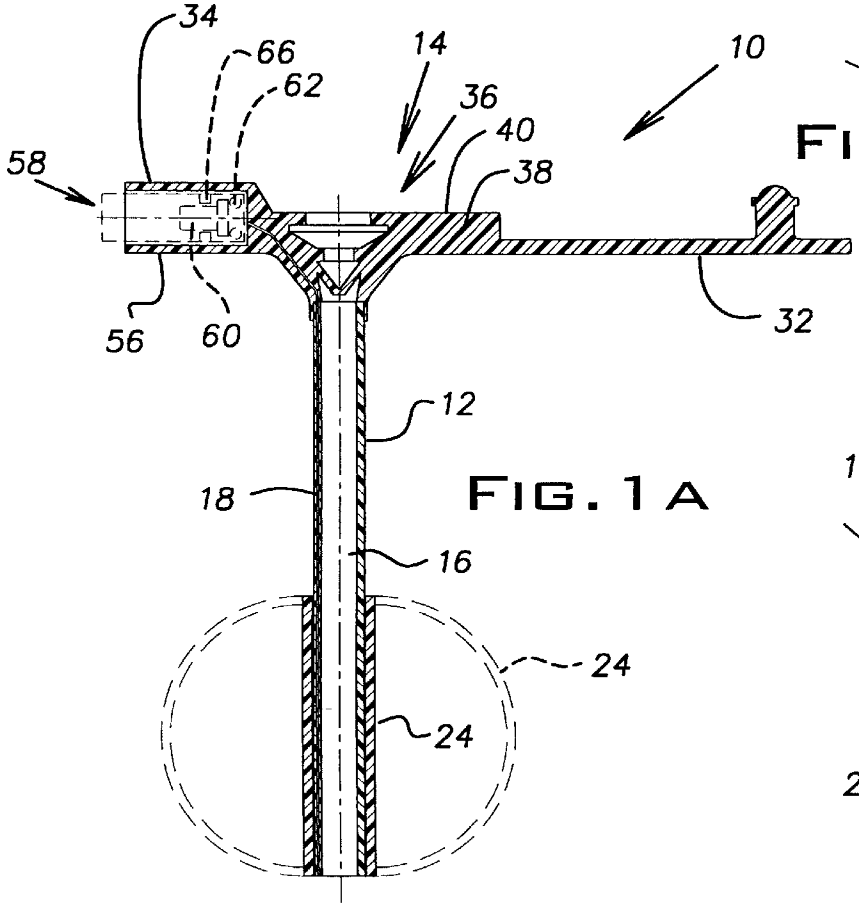
FIG. 1*a* is a front, cross-sectional view of a low profile balloon feeding device according to the present invention.

With reference to FIGS. 1*a*–1*d,* a low profile balloon feeding device 10 according to the present invention is illustrated. The feeding device 10 includes an elongated tubular member 12 and a bolster portion 14, as illustrated.

The tubular member 12 includes a feeding lumen or passage 16 and an inflation lumen or passage 18. Preferably, the feeding and inflation passages 16, 18 extend longitudinally the length of the tubular member 12. The feeding passage 16 is generally coaxial with an axis of the tubular member 12. The inflation passage 18 is parallel to, but offset laterally from, the feeding passage 16, as illustrated.

Figure 1D:
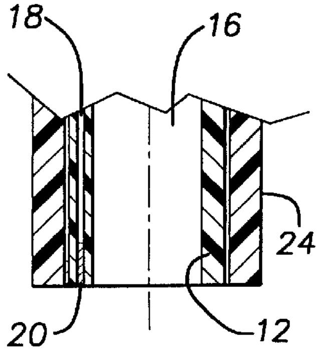
FIG. 1*d* is an enlarged sectional view of a lower portion of the tubular member of the feeding device shown in FIG. 1*a;*

Preferably, a lower end of the inflation lumen 18 is blocked by a plug 20 (FIG. 1*d*). A lateral or radially opening bore 22 (FIG. 1*c*) through the tubular member 12 and into the inflation passage 18 is provided to permit fluid to flow between the inflation passage 18 and a balloon member 24 which radially surrounds the tubular member 12. The balloon member 24 is cylindrical or tubular in shape when deflated or at-rest, and the bottom and top portions of the balloon member are sealed to the tubular member 12, as is well known in the art. The balloon member is inflated (deflated) by introduction (removal) of air, saline, or other fluid into the balloon member 24 via the inflation passage 18 and the bore 22, as is well known in the art. The balloon member in an inflated state is shown in dashed lines in FIG. 1*a*.

Figure 2C:
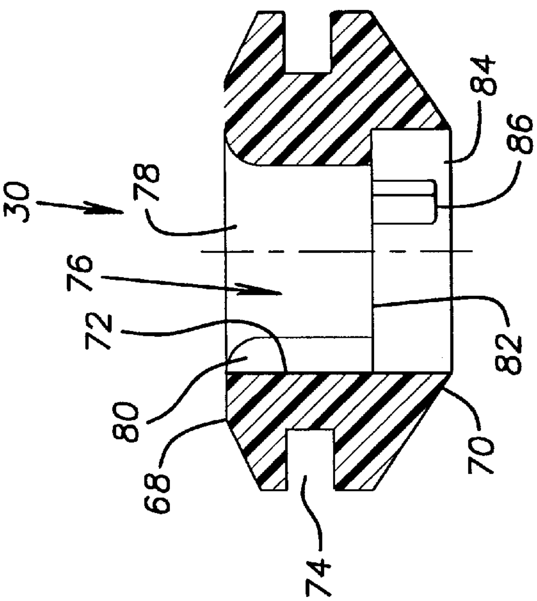
FIG. 2*c* is a cross sectional view of the locking cap shown in FIGS. 2*a* and 2*b*, as seen along line 2*c*–3*c* of FIG. 2*b;*
Figure 2B:
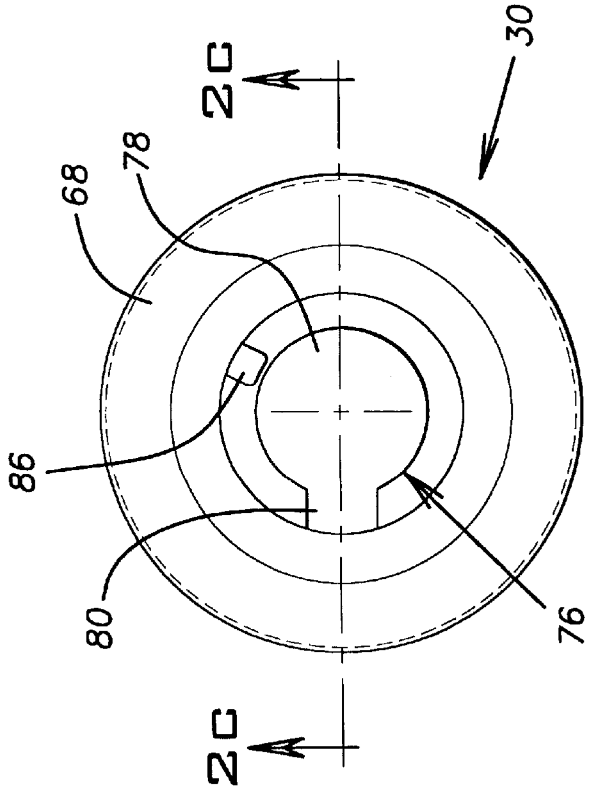
FIG. 2*b* is a top plan view of the locking cap shown in FIG. 2*a;*
Figure 2A:
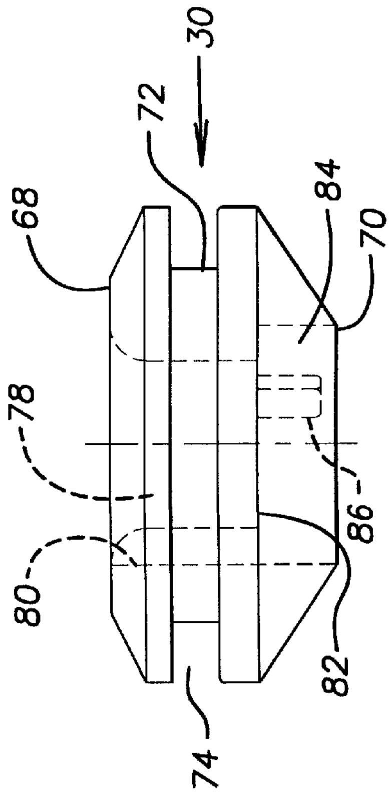
FIG. 2*a* is a front elevational view of a locking cap member used with the feeding device according to the present invention.
Figures 3A, 3B, 3C, 3D:
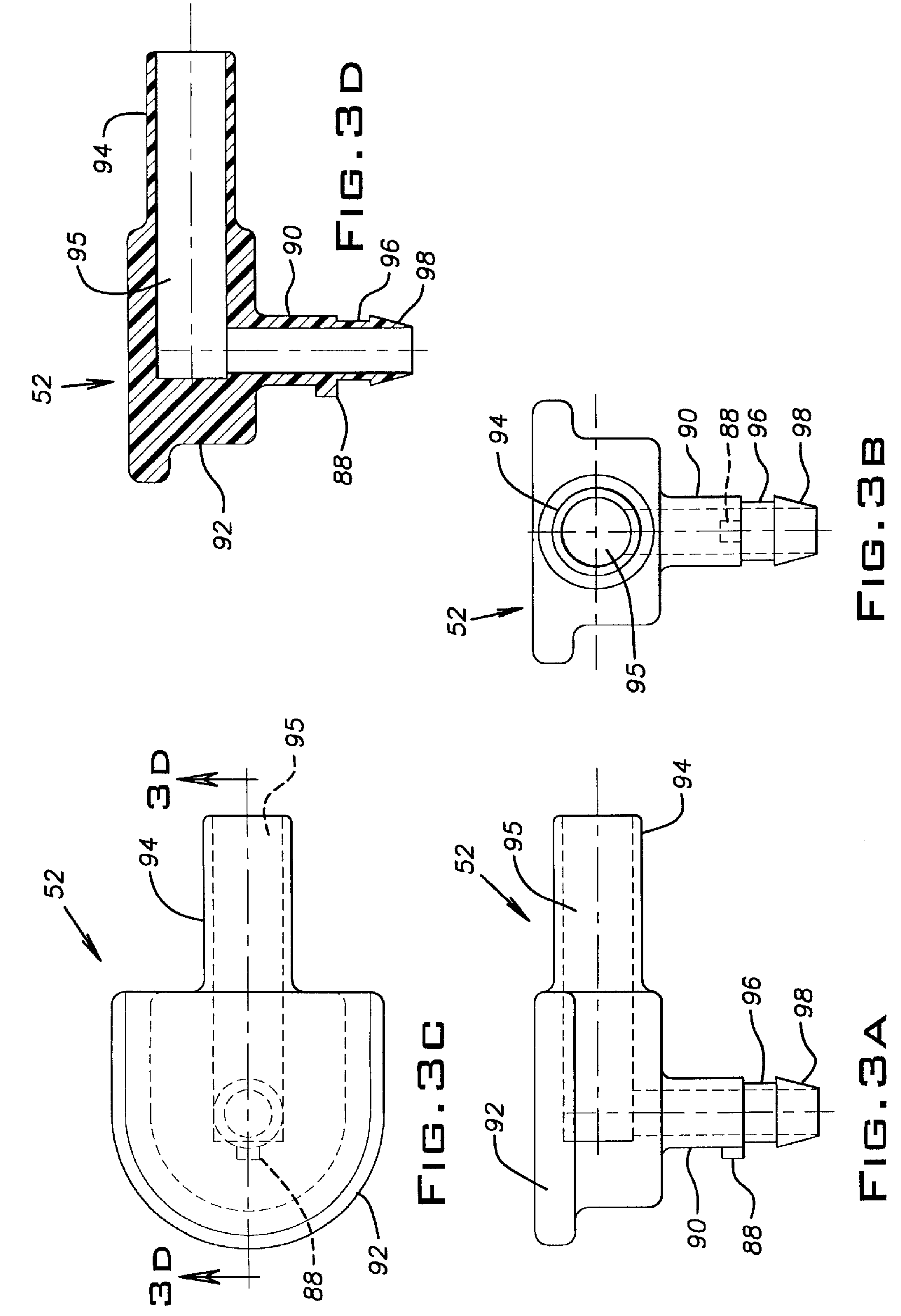
FIG. 3*a* is a front elevational view of a feeding adapter used in conjunction with the feeding device according to the present invention.
FIG. 3*b* is an end elevational view of the feeding adapter shown in FIG. 3*a;*
FIG. 3*c* is a top plan view of the feeding adapter shown in FIGS. 3*a* and 3*b;*
FIG. 3*d* is a cross sectional view of the feeding adapter as seen along line III—III in FIG. 3*c;*
Figure 4C:
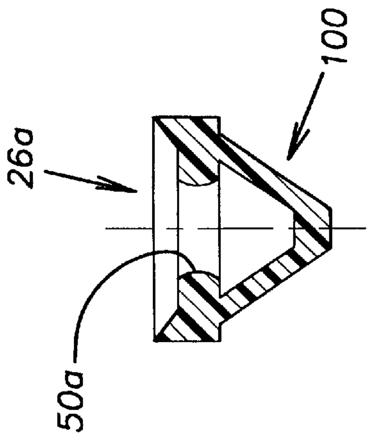
FIG. 4*c* is a cross-sectional view of the alternative anti-reflux valve as seen along line 4*c*—4*c* of FIG. 4*b;*
Figure 4B:
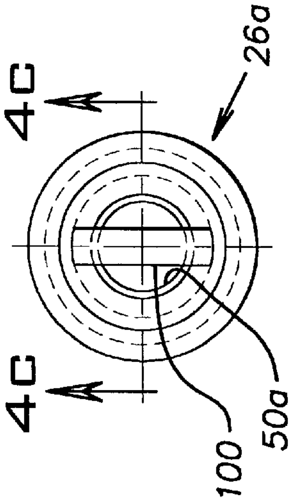
FIG. 4*b* is a top plan view of the alternative anti-reflux valve shown in FIG. 4*a;*
Figure 4A:
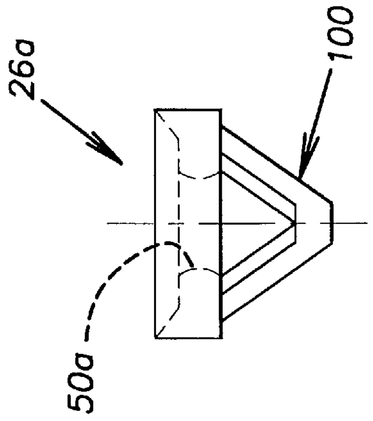
FIG. 4*a* is a front elevational view of an alternative anti-reflux valve used in conjunction with a second embodiment of the present invention.
Figure 4D:
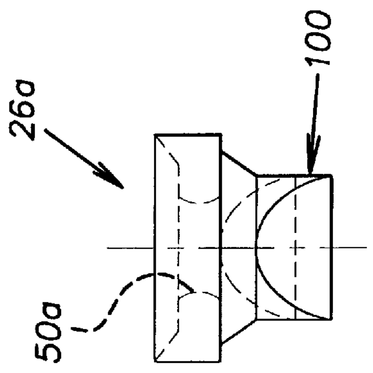
FIG. 4*d* is a side elevational view of the alternative anti-reflux valve according to the present invention.

The inflation passage 18 and feeding passage 16 extend through the bolster portion 14. Generally, at the juncture or union of the bolster portion 14 and the tubular member 12, as shown in FIG. 2, the feeding passage 16 is closed by an anti-reflux valve 26. Relatively above the anti-reflux valve 26, the feeding lumen 16 defines a receptacle 28 for a locking cap member 30 (FIGS. 2*a*–2*c*), as will be described more fully hereinafter.

The bolster portion 14 includes, in addition to the anti-reflux valve 26, a closure member 32, an inflation valve housing 34, and a cap retainer portion 36. The cap retainer portion 36, inflation valve housing 34, and closure member 32 are at least partially provided by a continuous wall member 38, as illustrated.

The cap retainer portion 36 provides the receptacle 28 for the locking cap member 30. The retainer portion includes the wall member 38 which has a generally planar outer surface 40, and a radial wall 42 having an inner surface which defines a portion of the feeding passage and generally conforms to the peripheral shape of the locking cap member 30, to be described hereafter. The outer surface is penetrated by an opening 44 for the feeding passage 16. An annular rib 45 surrounds the opening 44 and serves to retain the cap member 30 within the receptacle 28. The feeding passage opening 44 at the outer surface 40 has a first, relatively larger, diameter as compared to the diameter of the feeding passage 16 within the tubular member 12.

With reference to FIG. 1*b*, relatively below the wall member outer surface 40, the radial wall 42 defines receptacle 28 which receives and retains a portion of the locking cap member 30. More specifically, the receptacle 28 is defined by an annular wall portion 46 and a frustoconical wall portion 48. The annular wall portion 46 defines a cylindrical space having a second diameter. The second diameter is larger than the first diameter of the feeding passage opening 44 at the wall member 38.

The frustoconical wall portion 48 extends downwardly from the annular wall portion 46. A larger diameter end of the frustoconical wall portion 48 is adjacent the annular wall portion 46 and the smaller diameter end of the frustoconical wall portion 48 is remote and spaced from the annular wall portion 46. The size of the smaller diameter end of the frustoconical wall portion 48 is slightly less than the diameter of the feeding passage opening 44 at the wall member 38, as illustrated in FIG. 1*b*.

The smaller diameter end of the frustoconical wall portion 48 merges with an annular seal member 50 which defines a lower extent of the locking cap member receptacle 28. The seal member 50 extends into the feeding lumen 16 and defines an opening having a third diameter. The third diameter is the smallest portion of the feeding lumen 16, with the exception of the anti-reflux valve 26. The sealing member 50 is located immediately vertically adjacent the anti-reflux valve 26, (i.e., between the locking cap member 30 which is received within the receptacle 28 and the anti-reflux valve 26) and cooperates with a feeding adapter 52 to help locate and seal the feeding adapter 52 within the feeding lumen 16, as will be discussed more fully hereafter.

The anti-reflux valve 26 is integrally formed with the bolster portion 14 in the first preferred embodiment of the present invention illustrated in FIGS. 1*a*–1*d*. The anti-reflux valve 26 in the preferred and illustrated embodiment is a duck-bill type valve having a plurality of flexible arm members. Preferably, two arm members are provided, each of the arm members integrally extending from the bolster portion relatively beneath the sealing member 50 and at an angle to the longitudinal axis of the tubular member 12.

The inflation passage 18 curves as it passes through the bolster portion 14 between the inflation valve housing 34 and the tubular member 12. A generally constant thickness of material is maintained between the inflation passage 18 and the receptacle 28 as the inflation passage curves toward the inflation valve housing 34 to prevent distortion and compression of the inflation passage by forces applied to the cap member 30, as will be described more fully hereinafter. The inflation passage 18 extends from a base wall 54 of the valve housing 34, through the bolster portion 14, and into and through the tubular member 12.

The inflation valve housing 34 includes a cylindrical wall 56 which extends upwardly parallel to the wall member 38 and laterally in a direction generally opposite or away from the closure member 32, as illustrated. The base wall 54 of the valve housing 34 is generally perpendicular to the wall member 38. Relatively beneath the cylindrical wall 56, the wall member 38 provides a generally planar lower surface which is co-planar with a lower surface of the cap retainer portion 36 radially surrounding the tubular member 12. As such, the lower surface of the wall member 38 defines a support surface which engages an exterior body surface during use of the feeding device 10, as will be apparent to one skilled in the art.

The inflation valve housing 34 is adapted to sealingly receive an inflation valve 58. The inflation valve 58 (shown in dashed lines in FIG. 1*a*) is sealing secured within the inflation valve housing 34 by silicone-based adhesive, or other well known sealing means. The inflation valve 58 preferably includes a check valve plunger 60 which is biased by a spring 62 to a closed position preventing fluid flow out of the balloon member 24. The plunger 60 is mounted in a plastic valve housing 64 and is manually moved in a longitudinal direction against the spring bias away from a housing-provided seat 66 to an unseated or open position permitting fluid flow therepast. Numerous interchangeable valves of this type are commercially available and known in the art and, therefore, the inflation valve will not be discussed further herein.

The locking cap member 30 is preferably a one-piece molded part, and is illustrated in FIGS. 2*a*–2*c*. The cap member 30 includes upper and lower ring-shaped wall members 68, 70 which are joined by a cylindrical interconnecting wall 72. The upper wall member 68 includes an annular upper surface which slopes downwardly and outwardly. The lower wall member 70 has a frustoconical outer surface which merges into a short annular vertical surface. As such, the lower wall member 70 has a peripheral shape which generally conforms to the shape of the receptacle 28 formed in the bolster portion 14, and is designed to be received within the receptacle 28, as will be defined more fully hereinafter. In this regard it is important to note that the frustoconical outer surface of the lower wall member 70 permits a reduction in the thickness of the bolster portion 16 while maintaining an appropriate thickness between the cap member and the bottom surface of the wall member 38. The reduced height dimension of the cap member 30 at the lateral sides thereof provided by the angled or frustoconical surface of the lower wall member 70 reduces the lateral height dimensions of the receptacle 28, and thereby increases the material thickness at these areas. As such, the shape of the cap member 30 permits the feeding device 10 according to the present invention to have a lower profile than would otherwise be possible.

An annular peripheral groove 74 is formed or defined between the upper and lower wall members 68, 70 and radially outward of the interconnecting wall 72. The annular groove 74 is shaped and dimensioned to receive the annular rib 45 surrounding the feeding passage opening 44 in the bolster portion 14. As such, the upper wall member 68 abuts the outer surface 40 of the wall member 38 and overlies and surrounds the feeding lumen opening 44. The annular rib 45 is trapped between the upper and lower wall members 68, 70.

An inner surface of the cap member 30 defines a keyway or locking adapter receptacle 76 into which the feeding adapter 52 can be inserted and removably secured in a push-and-twist-to-lock fashion.

The keyway 76 has a cylindrical main passageway 78 and a generally square slot 80, as shown best in FIG. 2*b*. A radially inward extending wall 82 defines a bearing or support surface, as will be described hereinafter. A circular recess 84 is formed in the lower wall member 70 relatively beneath the wall 82 coaxial with the passageway 78, and extends downwardly from the passageway 78. A radius of the circular recess 84 is approximately equal to a radius of the cylindrical main passageway 78 plus the radial depth of the square slot 80.

A stop member 86 projects radially inwardly and integrally from the inner surface of the lower wall member 70 and into the circular recess 84. The stop member 80 projects radially inward from the lower wall member inner surface a distance generally identical to the radial depth of the square slot 80. The stop member 86 is radially offset relative to the square slot 80 such that the adapter 52, to be described hereafter, can be inserted into the keyway 76 and turned a predetermined amount before engaging the stop member 86. As such, the circular recess 84 defines a receptacle in which a portion of the feeding adapter is received and rotatably secured.

When the adapter 52 is inserted into the cap member 30 and rotated such that a key portion 88 of the adapter is radially offset or out of alignment with the square slot 80, the adapter is vertically retained within the locking cap member 30 by engagement of the key 88 with the wall 82, and is prevented from being moved axially or longitudinally. In the preferred and illustrated embodiment, the stop member 86 is radially offset, in a clockwise direction, between about 90° to about 180° from the square slot 80. More preferably, the stop member 86 is radially offset, in a clockwise direction, between about 110° and 130° and, most preferably, is radially offset, in a clockwise direction, from the square slot 80 about 120°, as illustrated.

The feeding adapter 52 shown in FIGS. 3*a*–3*d*, cooperates with the locking cap member 30 to define a locking means which securely fastens the feeding adapter 52 to the locking cap member 30. The feeding adapter 52 also cooperates with the sealing member 50 and the anti-reflux valve 26 to seal a lower dispensing portion 90 of the feeding adapter to the feeding device. It should be apparent that various different configurations of feeding adapters could be used with the feeding device according to the present invention. For example, the preferred and illustrated feeding adapter is identified as a 90° adapter, and is preferred due to its low profile which limits the projection of the device from the feeding device which is desirable from an aesthetic and functional viewpoint for the user. Alternative designs, such as ones wherein the adapter extends generally coaxial with the tubular portion of the feeding device, are envisioned.

The preferred feeding adapter 52 includes the lower dispensing portion 90 which extends downwardly from a body member 92. A connecting portion 94 extends laterally from the body member 92 and generally perpendicular to the dispensing portion 90. A passage 95 is formed through the feeding adapter from the connector portion 94, body portion 92, and the dispensing portion 90, as illustrated.

The dispensing portion 90 is generally elongated and tubular in shape, but includes the key or tab 88 extending radially therefrom. The dispensing portion 90 also includes a radial or annular groove 96. The groove 96 is located relatively below the key 88, as illustrated. A lower terminal end 98 of the dispensing portion 90 is beveled or frustoconical such that the dispensing portion 90 narrows toward the lower end thereof.

The key 88 is adapted to be slidably inserted into the square slot 80 of locking cap member 30 as the dispensing portion 90 is simultaneously inserted through the cylindrical main passageway 78. When the dispensing portion 90 is fully inserted into the locking cap member 30, the lower terminal end 98 of the dispensing portion 90 extends into and opens the anti-reflux valve 26 while the radial groove 96 receives the sealing member 50. As such, after rotation of the feeding adapter 52 to move the key 88 out of alignment with the slot 80 and thereby prevent unintended removal of the feeding adapter 52 from the cap member 30 due to the key 88 engaging the wall 82, the introduction of fluids through the passage 95 and the feeding passage 16 may commence. The liquids are directly installed into the feeding lumen relatively after or downstream of the anti-reflux valve 26, and a double seal is provided to prevent undesirable backflow of liquid outwardly through the locking cap member 30 and the bolster portion 16. The double seal is provided by the sealing engagement between the terminal end 98 of the dispensing portion 90 and the anti-reflux valve 26 and the sealing engagement between the sealing member 50 and the radial groove 96 of the dispensing portion 90.

A separate anti-reflux valve 26*a* is shown in FIGS. 4*a*–4*d* and forms a portion of a second embodiment of the present invention. The anti-reflux valve 26*a* is intended to be separately formed and thereafter permanently installed into a feeding device generally as illustrated in FIGS. 1*a*–1*d*, except as noted hereinafter. The main modification to the previously described feeding device is the fact that the sealing member 50 and anti-reflux valve are removed or not present in the feeding device according to the second embodiment of the present invention to permit insertion or installation of the anti-reflux valve shown in FIGS. 4*a*–4*d*. Therefore, as will be apparent from the brief description to follow, the separate anti-reflux valve 26*a* is generally identical from a functional point of view as the previously described sealing member 50 and anti-reflux valve 26.

The anti-reflux valve 26*a* includes a valve member 100, a sealing member 50*a*. The sealing member 50*a* is ring-shaped and is sealingly received within the annular groove 96 of the dispensing portion 90 of the feeding adapter 52. The valve member 100 is engaged and opened by the terminal end 98 of the dispensing portion 90.

While the preferred embodiments of the present invention have been described herein, it is clear that the present invention is not limited thereto. Rather, the invention is capable of numerous modifications and substitutions of parts without departing form the scope and spirit of the present invention as defined by the claims appended hereto.

What is claimed is:

1. A gastrostomy feeding device comprising a bolster portion, a balloon member, and a tubular member extending between said bolster portion and said balloon member, said tubular member and bolster portion cooperating to define an inflation passage and a feeding passage, said inflation and feeding passages extending through said tubular member generally parallel one another and to a longitudinal axis of said tubular member, said bolster portion comprising an anti-reflux valve, an inflation valve housing, a receptacle, and a feeding port, said inflation valve housing receiving an inflation valve and being in fluid communication with said balloon member via said inflation lumen, said receptacle receiving a locking cap member, said cap member being disposed relatively between said feeding port and said anti-reflux valve, wherein said inflation lumen curves as it extends through said bolster portion from said tubular member toward said inflation valve housing to maintain a generally constant thickness of material between said inflation lumen and said receptacle to reduce distortion of the inflation passage by forces applied to the cap member, and wherein said bolster portion further includes a closure member, said closure member having a first end secured to the bolster portion and a second end including a plug which is received within the cap member.

2. A gastrostomy feeding device according to claim 1, further comprising a feeding adaptor, wherein said cap member defines a keyway and said feeding adaptor defines a key, said feeding adaptor key being received within and removably locked to said keyway in a twist-and-lock fashion.

3. A gastrostomy device according to claim 1, wherein said receptacle is provided by a cap retainer portion of said bolster portion, said receptacle being defined by a pair of annular wall surfaces and a radial wall, said radial wall surrounding and corresponding to at least a portion of said cap member.

4. A gastrostomy device according to claim 3, wherein said radial wall includes an annular wall portion and a frustoconical wall portion, said annular wall portion defining a cylindrical space and said frustoconical wall portion extending downwardly from said annular wall portion.

5. A gastrostomy device according to claim 4, wherein an annular seal member is disposed relatively beneath said frustoconical wall portion, said seal member defining a lower extent of said receptacle.

6. A gastrostomy device according to claim 5, wherein said cap retainer portion includes an outer wall, said outer wall being penetrated by an opening, said outer wall defining an upper limit of said receptacle.

7. A gastrostomy device according to claim 6, wherein said anti-reflux valve is located vertically adjacent said seal member.

8. A gastrostomy device according to claim 7, wherein said anti-reflux valve is integrally formed with the bolster portion and includes a plurality of flexible arms.

9. A gastrostomy feeding device comprising a bolster portion, a balloon member, and a tubular member extending between said bolster portion and said balloon member, said tubular member and bolster portion cooperating to define an inflation passage and a feeding passage, said inflation and feeding passages extending through said tubular member generally parallel one another and to a longitudinal axis of said tubular member, said bolster portion comprising an anti-reflux valve, an inflation valve housing, a receptacle, and a feeding port, said inflation valve housing receiving an inflation valve and being in fluid communication with said balloon member via said inflation lumen, said receptacle receiving a locking cap member, said cap member being disposed relatively between said feeding port and said anti-reflux valve, wherein the cap member comprises upper and lower ring-shaped wall members that are joined by a cylindrical interconnecting wall, said upper and lower ring-shaped wall members extending radially outward farther than said cylindrical interconnecting wall;

wherein said receptacle is defined at least in part by a radial wall surrounding and corresponding to at least a portion of said cap member, said radial wall including an annular wall portion and a frustoconical wall portion, said annular wall portion defining a cylindrical space and said frustoconical wall portion extending downwardly from said annular wall portion;

wherein said gastrostomy device further comprises an annular seal member disposed relatively beneath said frustoconical wall portion, said seal member defining a lower extent of said receptacle;

wherein said anti-reflux valve is located vertically adjacent said seal member;

wherein said cap retainer portion includes an outer wall, said outer wall being penetrated by an opening, said outer wall defining an upper extent of said receptacle;

wherein said bolster portion further includes a closure member, said closure member having a first end secured to the bolster portion and a second end including a plug which is received within the cap member; and wherein said gastrostomy feeding device further comprises a feeding adaptor, wherein said cap member defines a keyway and said feeding adaptor defines a key, said feeding adaptor key being received within and removably locked to said keyway in a twist-and-lock fashion.

10. A gastrostomy feeding device comprising a bolster portion, a balloon member, a feeding adaptor, and a tubular member extending between said bolster portion and said balloon member, said tubular member and said bolster portion cooperating to define an inflation passage and a feeding passage, said inflation and feeding passages extending through said tubular member generally parallel one another and to a longitudinal axis of said tubular member, said bolster portion comprising an anti-reflux valve, an inflation valve housing, a receptacle, an annular seal member, and a feeding port, said inflation valve housing receiving an inflation valve and being in fluid communication with said balloon member via said inflation lumen, said receptacle receiving a locking cap member, said cap member being disposed relatively between said feeding port and said anti-reflux valve, wherein said anti-reflux valve is integrally formed with said bolster portion and comprises a plurality of flexible arm members, and wherein said seal member is disposed relatively between said cap member and said anti-reflux valve, and wherein said cap member defines a keyway and said feeding adaptor comprises a key, said feeding adaptor key being received within and removably locked to said cap member keyway in a twist-and-lock fashion.

11. A gastrostomy feeding device according to claim 10, wherein said feeding adaptor comprises a dispensing portion which is adapted to extend through said cap member and beyond said anti-reflux valve and into said tubular member, said dispensing portion defining an annular groove which sealing receives said seal member.

* * * * *

UNITED STATES PATENT AND TRADEMARK OFFICE

CERTIFICATE OF CORRECTION

PATENT NO. : 6,019,746

DATED : February 1, 2000

INVENTOR(S) : Picha et al.

It is certified that error appears in the above-indentified patent and that said Letters Patent is hereby corrected as shown below:

On the title page:

Item [56] References Cited, U.S. DOCUMENTS, insert --5,458,583 10/1995 McNeely et al.--.

Column 2, Line 43, delete "2c-3c" and insert --2c-2c--.

Column 2, Line 52, delete "III-III" and insert --3d-3d--.

Signed and Sealed this

Twentieth Day of February, 2001

Attest:

Nicholas P. Godici

NICHOLAS P. GODICI

Attesting Officer

*Acting Director of the United States Patent and Trademark Office*